United States Patent
Tao

(10) Patent No.: US 9,045,448 B1
(45) Date of Patent: Jun. 2, 2015

(54) METHODS FOR CONVERTING CARBOHYDRATES INTO OXYGENATED HYDROCARBONS

(71) Applicant: Thomas Tao, Hopkinton, MA (US)

(72) Inventor: Thomas Tao, Hopkinton, MA (US)

( * ) Notice: Subject to any disclaimer, the term of this patent is extended or adjusted under 35 U.S.C. 154(b) by 0 days.

(21) Appl. No.: 14/145,958

(22) Filed: Jan. 1, 2014

Related U.S. Application Data

(60) Provisional application No. 61/748,725, filed on Jan. 3, 2013.

(51) Int. Cl.
| | |
|---|---|
| *C07C 27/26* | (2006.01) |
| *C07D 307/46* | (2006.01) |
| *C07D 307/20* | (2006.01) |
| *C07C 51/00* | (2006.01) |
| *C07C 45/60* | (2006.01) |
| *C07C 29/132* | (2006.01) |

(52) U.S. Cl.
CPC ............ *C07D 307/46* (2013.01); *C07D 307/20* (2013.01); *C07C 51/00* (2013.01); *C07C 45/60* (2013.01); *C07C 29/132* (2013.01)

(58) Field of Classification Search
USPC .................................................. 568/920, 921
See application file for complete search history.

(56) References Cited

U.S. PATENT DOCUMENTS 4,523,928 A * 6/1985 Hillman et al. ................ 44/451

OTHER PUBLICATIONS

Yang et al. Carbohydrate Research (1996), 280(1), 47-57.*
Yang et al. Carbohydrate Research (1996), 280(1), 27-45.*

* cited by examiner

*Primary Examiner* — Nizal Chandrakumar
(74) *Attorney, Agent, or Firm* — David P. Lentini

(57) ABSTRACT

Methods for efficiently converting carbohydrates into various oxygen-containing hydrocarbon derivatives, including straight-chain and cyclic aldehydes, ketones, alcohols, acids, and heteroaromatic compounds, are described and provided. In some embodiments, the methods include combining a carbohydrate with a material having a high affinity for carbon dioxide in stoichiometric amounts and heating said combination at temperature effective to cause de-carbonation of the carbohydrate and the formation of the products. In more specific embodiments, the material is calcium oxide (CaO) and the carbohydrate is sucrose, and the reaction is performed at temperatures between about 150° C. and about 450° C.

17 Claims, 3 Drawing Sheets

METHODS FOR CONVERTING CARBOHYDRATES INTO OXYGENATED HYDROCARBONS

CROSS REFERENCE TO PRIOR APPLICATION

This application claims priority under 35 U.S.C. 119(e) from Provisional U.S. Patent Application Ser. No. 61/748,725, entitled CHEMICAL DECARBONATION OF CARBOHYDRATES TO GASES AND LIQUIDS, filed 3 Jan. 2013, the disclosure of which is incorporated herein by reference in its entirety and for all purposes.

FIELD OF THE INVENTION

The present invention relates to methods converting carbohydrates into hydrocarbons and oxygenated hydrocarbons (i.e., ketones and aldehydes) with reduced formation of char. The methods of the invention include reacting utilizing a metal oxide or metal hydroxide of the alkaline, alkaline earth, or rare alkaline earth metals which is basic and has a strong chemical affinity for carbon dioxide, as a stoichiometric reactant. The present invention has applications in the fields of organic chemistry, petroleum chemistry, and biofuels.

BACKGROUND OF THE INVENTION

Carbohydrates, also known as saccharides, are the dominant chemical constituents of the most abundant and dominant biomasses on earth, which comprise more than 60% of the total known plant mass. Common carbohydrates include sugars, starches, cellulose, and hemicelluloses, and their various chemical derivatives. Carbohydrates have the general chemical formula: $C_m(H_2O)_n$ where the hydrogen and oxygen are in a ratio of 2:1 as for water (whence the name "hydrate of carbon", since the constituents of water, hydrogen (H) and hydroxyl (OH), are bound to each carbon atom). Carbohydrates are neither chemical hydrates nor fatty acids; instead, they are polyhydroxyl-, aldehyde-, and ketone-containing compounds.

The carbohydrates are divided into four chemical groupings: monosaccharides, disaccharides, oligosaccharides, and polysaccharides. In general, the monosaccharides and disaccharides are commonly referred to as "sugars". A common example of a monosaccharide is glucose, and common examples of disaccharides are sucrose and lactose. Oligosaccharides are chains of fewer than ten saccharides; polysaccharides are chains longer than ten saccharides. Biologically, polysaccharides serve for the storage of energy (e.g., starch and glycogen) and as structural support (e.g., cellulose and hemicellulose in plants and chitin in arthropods).

Cellulose has a formula of $(C_6H_{10}O_5)_n$. It is a polysaccharide consisting of a linear chain of several hundred to over ten thousand β(1→4) linked D-glucose units. Cellulose is the primary structural component of the cell wall of green plants, such as in many forms of algae and the oomycetes. Cellulose is both abundant and renewable. About 33% of all plant matter is cellulose, although the percentage may be higher in some plants, such as 90% in cotton and 40-50% in trees.

Another major carbohydrate is hemicellulose. Hemicellulose is a polysaccharide, consisting of various sugars. About 20% of all plant biomass is hemicellulose. As such, hemicellulose is both abundant and renewable.

Historically, harnessing this vast chemical resource has been done biologically, i.e., using microbes and other organisms to convert carbohydrates into other useful chemicals. In particular decarbonation of carbohydrates to make alcohol is traditionally accomplished by fermentation, such as by wine making and brewing beer. New technologies have emerged over the last several decades to convert carbohydrates or general biomass into other useful chemicals, especially hydrocarbons and related compounds, including liquid biodiesel, bioethanol, and bio-oils, using fermentation; dehydration, pyrolysis (including flash pyrolysis; see Bridgewater, "Principles and practice of biomass fast pyrolysis processes for liquids," *J. Anal. Appl. Phys.* 51, 3-22 (1999) and Bartek (U.S. Pat. No. 8,236,173)); and gasification into to syngas (i.e., synthetic gas) by partial oxidation, followed by a Fischer Tropsch process to make hydrocarbons (see, e.g., Chronet, U.S. Pat. No. 8,137,655).

The ability to derive hydrocarbons and oxygenated hydrocarbons from carbohydrates could provide an important source of important chemical building blocks and fuels from renewable sources, especially during a time when the supply of geological hydrocarbons is increasingly uncertain. Nevertheless, despite all the advances with these traditional technologies, the production of hydrocarbons and oxygenated hydrocarbons from carbohydrate feedstocks is not efficient. Fermentation is a slow, sometimes inefficient process. Dehydration, pyrolysis, and gasification into a Fischer Tropsch process or bio-oils creates a large amount of char and other waste products (and thus wastes feedstock), and is energy intensive. As such, all the art standard techniques are unacceptable.

Therefore, it would be advantageous to develop new methods to produce hydrocarbons and oxygenated hydrocarbons from carbohydrates, such as sugars, cellulose and hemicellulose, without creating large amounts of char or other waste products or using large amounts of energy. Due to their high abundance and renewability, using carbohydrates as a feedstock could create a "green" solution to the world's energy and chemical needs. But there are a few problems associated with trying to use carbohydrates as precursors to fuels and chemicals. The present invention meets these and other needs.

BRIEF DESCRIPTION OF THE INVENTION

The present invention provide the surprising and unexpected discovery that performing decarbonation reactions on carbohydrates using a reagent with a high affinity for $CO_2$ in stoichiometric amounts provides for low and moderate temperature reactions of carbohydrate feedstock to form an organics stream containing oxygenated hydrocarbons rich in ketones, and aldehydes among other valuable products. More particularly, in some embodiments, the invention produces acetone, butanone, various flavors and fragrances (such as diacetyl, acetoin, acetol, acetol acetate, furaneol, and corylone), and various furfurals, cyclopentenones, and furans, in yields of between about 65% and about 80%, at temperatures of between about 165° C. and about 300° C., and over reaction periods of a few minutes to a few hours. Little dehydration and charring is observed. The desire to directly create organics from carbohydrate feedstock via a chemical process is a longstanding need that has previously gone unsolved. The present invention solves this problem in the art.

In a first aspect, the present invention provides methods for the de-carbonation of a carbohydrate to form one or more alcohol, aldehyde, ketone, or organic acid products therefrom, comprising: combining a carbohydrate with a material having a high affinity for carbon dioxide in stoichiometric amounts and heating said combination at temperature effective to cause de-carbonation of said carbohydrate and the formation of said products.

In some embodiments, carbohydrate is selected from the group consisting of: mono-, di-, oligo-, and poly-saccharides, starches, cellulose, hemicellulose, and lignocelluosic biomass. In more specific embodiments, material is selected from the group consisting of: oxides and hydroxides of the alkaline, alkaline-earth, or rare alkaline-earth metals.

Among the more specific embodiments just described are those in which the carbohydrate and the material are combined in a material:carbohydrate ratio of between about 0.5:1 and about 2:1 by stoichiometry. Still more specific embodiments are those further wherein the temperature is between about 150° C. and about 450° C., more specifically between about 165° C. and about 300° C., yet more specifically between about 165° C. and about 250° C., and even more specifically between about 165° C. and about 200° C.

In other more specific embodiments, the material is an alkaline earth oxide, more specifically calcium oxide (CaO). Among the more specific embodiments just described are those in which the carbohydrate and the material are combined in a material:carbohydrate ratio of between about 0.2:1 and about 5:1 by stoichiometry. Still more specific embodiments are those further wherein the temperature is between about 150° C. and about 450° C., more specifically between about 165° C. and about 300° C., yet more specifically between about 165° C. and about 250° C., and even more specifically between about 165° C. and about 200° C.

In still other more specific embodiments, the carbohydrate is a di-saccharide; more specifically in some embodiments the di-saccharide is sucrose.

These, and still other features and advantages will become apparent when the following Detailed Description is read with the accompanying Drawings.

BRIEF DESCRIPTION OF THE DRAWINGS

The features of the present invention will best be understood from a detailed description of the invention and a preferred embodiment thereof selected for the purposes of illustration and shown in the accompanying drawings in which.

DETAILED DESCRIPTION OF SOME EMBODIMENTS OF THE INVENTION

Figure 1:
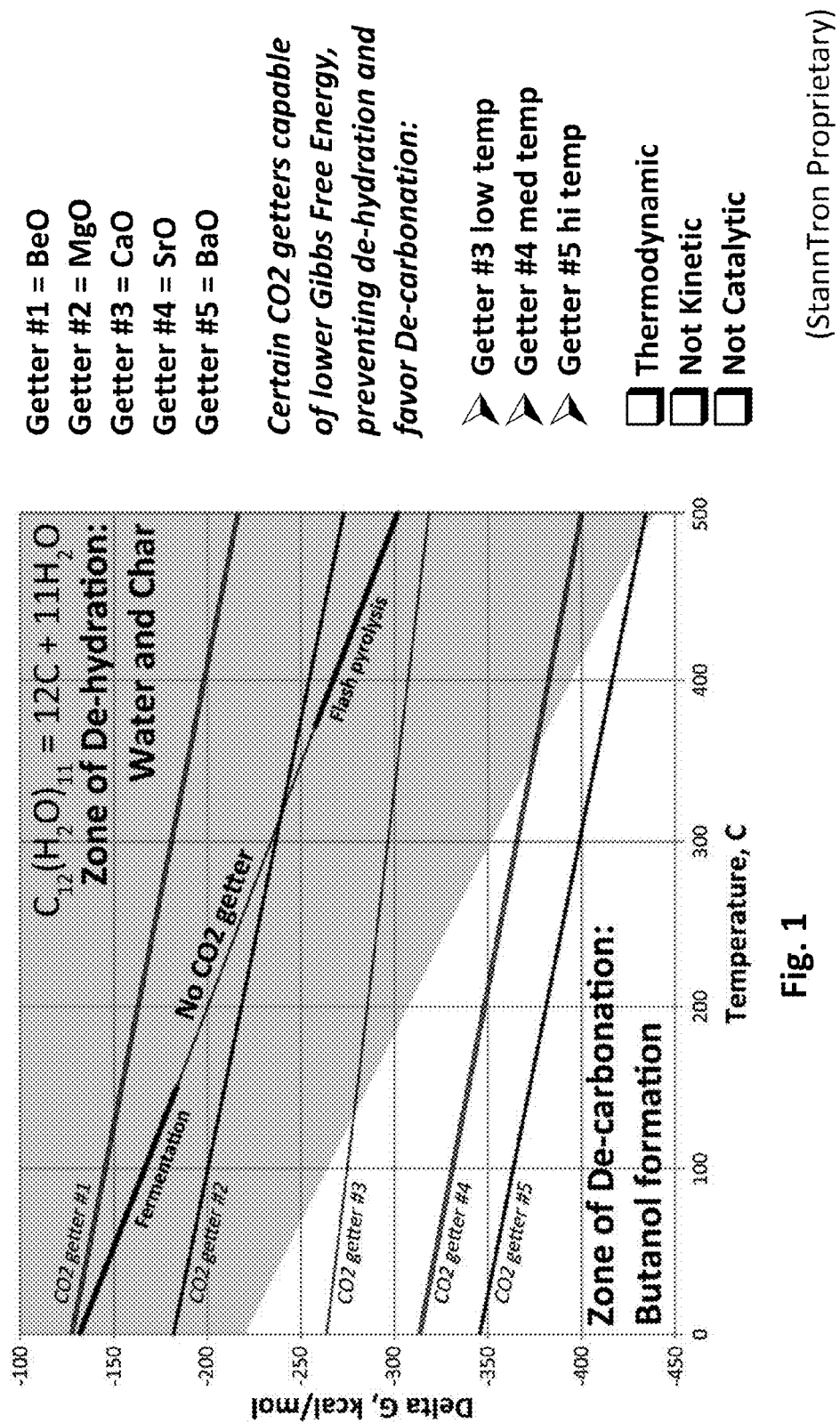
FIG. 1 illustrates a chemical decarbonation zone by plotting Gibbs free energy vs. temperature based on a sucrose reaction with reactants of metal oxides of Ba, Sr, Ca, Mg and Be at stoichiometric charges to form butanol and carbonates.

Chemical decarbonation is a chemical process in which a functional group of the form —$CO_2$ in a molecule is removed. The classic example is decarbonation of carboxylic acids by release of $CO_2$ from the acid (—COOH) at elevated temperatures or via a catalyst.

The present invention is very favorable because inter alia it can use any carbohydrate and is therefore very robust. It is not limited to simple carbohydrates, like fermentation reactions. Another advantage of the present invention is that it is a single chemical reaction, unlike Fischer-Tropsch based processes, that require synthesizing a syngas, then converting that syngas into a biofuel.

As noted above, any carbohydrate is useful in the present invention. Such compounds used can be mono-, di-, oligo-, and poly-saccharides, including sugars, starch, cellulose, hemicellulose, and lignocellulosic biomass. Preferred carbohydrates are sugars, cellulose, hemicellulose, and lignocellulosic biomass.

"Char" is a charcoal-type material produced by cooking organic matter in a low-oxygen environment. Char is produced commercially by pyrolysis reactions in amounts ranging from 15%-50% of the initial feedstock. Char contains varying amounts of carbon, hydrogen, and oxygen as well as ash and other impurities that, together with the structure, determine the properties.

A "reactant" is a material that has a high affinity to bind with, or otherwise sequester or scavange, $CO_2$ that does not chemically or otherwise interfere with the conversion of carbohydrate to organics. It is believed that the mechanism is that the reactant reduces the Gibbs Free Energy of a chemical reaction of carbohydrates. By altering the Gibbs Free Energy and other thermodynamics of the reaction, the reactants are able to make decarbonation to organics the preferred reaction, suppressing pyrolysis and dehydration. In practice, the reactant is generally (i) a metal oxide or metal hydroxide of the alkaline, alkaline earth, or rare alkaline earth metals, which is basic with a strong chemical affinity for carbon dioxide and/or (ii) a nitrogen-containing-heterocyclic-containing compound, such as imidazole, pyrazole, pyrrole, pyrazine, pyridazine, pyrimidine, pyridine, and their derivatives and ionic salts and/or (iii) basic chemicals of $NaAlO_2$, $Na_2SiO_3$. However, the inventor does not intend the term "reactant" to be limited to these compounds. In normal use, the reactant is consumed during the reaction but will be regenerated after the reaction. Further, while the reactants exemplified are regenerable, they need not be so for the invention to function as intended. They may be catalytic or merely consumed.

A preferred reactant is calcium oxide (CaO). Calcium oxide is converted to calcium carbonate ($CaCO_3$) during use in the present invention. The calcium carbonate can be harvested and thermally regenerated to create calcium oxide by a high temperature calcination reaction at 850° C.-900° C.

The loading of the reactant is a stoichiometric loading. This loading of reactant is relatively higher than similar chemicals are used in the prior art, primarily because they are not serving the same function. Without being bound to any particular theory of action, the high loading in the present provides substantial removal of $CO_2$ molecules to promote the decarbonation reaction. As the formula for carbohydrates is known to be $C_m(H_2O)_n$, a stoichiometric loading of reactant would be about one reactant molecule for every acetone formed as indicated in Equation (1), assuming each reactant reacts with stoichiometric $CO_2$ molecule and the goal is to remove oxygen in the form of $CO_2$ to preserve hydrogen. In considering the case of sucrose (formula $C_{12}H_{22}O_{11}$) forming acetone as indicated in equation (1), there would therefore be a 3:1 ratio of reactants to sucrose to get a stoichiometric loading of reactant. However, in practice there would be an access such as a 5:1 reactant to sucrose loading. In the case of cellulose, which can have over ten-thousand D-glucose units, using feedstock molecular weight becomes cumbersome and impractical. By way of example, consider cellulose with an average degree of polymerization of 5,000 units per molecule and varies. The monomer unit of cellulose is $C_6H_{10}O_5$. Therefore either using the monomer or the product in calculation of the stoichiometric becomes convenient, for example for every acetone produced, one needs to remove one $CO_2$ molecule. Of importance is the 1:1 stoichiometry between the functionalities of the reactant and the $CO_2$ molecule to be decarbonated. Therefore, by stoichiometric ratio (or when otherwise discussing stoichiometry), the inventor means a loading of reactant such that one molecule of reactant is present per two oxygen atoms in the form of $CO_2$ in the carbohydrate feedstock to be removed, assuming that the reactant only reacts with one unit of $CO_2$ from the carbohydrate feedstock. If the reactant is capable of reacting with a plurality of $CO_2$ molecules, that would naturally be taken into account as would be understood by the skilled artisan.

By "organics" in reference to the products of the method of the present invention, the inventor means organic fuels or biofuels or chemicals or biochemicals created by reacting carbohydrates with reactants. Through the inventor's experimentation, several organics have been identified as the result of the present invention, oxygenated hydrocarbons including acetone, methyl ethyl ketone, ethanol, acetic acid, propanonehydroxyl, butanol, various furans, hydroxyl methyl furfural, a number of food flavors, hydrocarbons, etc.

The resulting organics may be colorless, faint yellow, or another color. They are generally liquid or gas and may be volatile. Liquid organics are preferred products as they are more energy dense and more easily transported. They are useful as chemical stocks, food and beverage stocks, or energy stocks for transportation or heating fuels.

Figure 2:
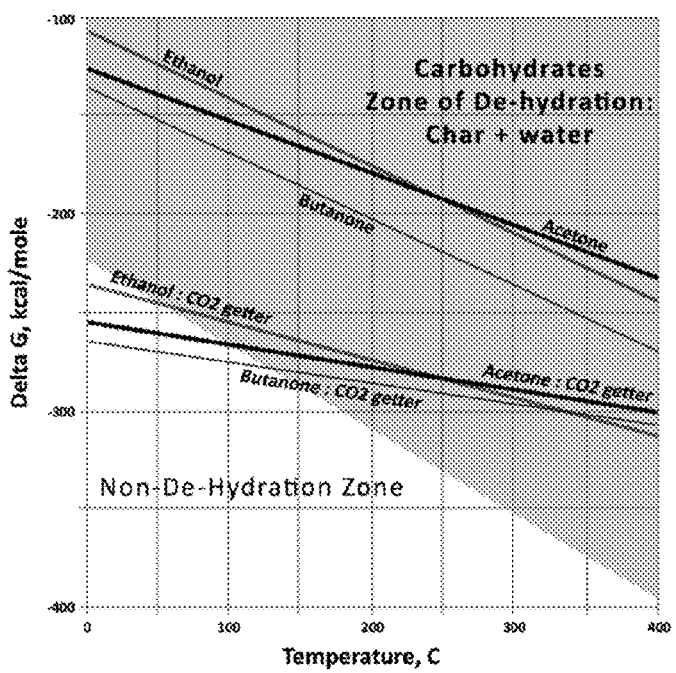
FIG. 2 illustrates zones of ketone formation from carbohydrates by decarbonation by plotting Gibbs free energy vs. temperature based on a surcose reaction with calcium oxide as a reactant to form ethanal, acetone, butanone, and carbonate.

In illustration of the concept and the thermodynamic principle of chemical decarbonation by removal of $CO_2$ from carbohydrates, the present invention discloses reactions in which sucrose ($C_{12}H_{22}O_{11}$) reacts with various metal oxides form metal carbonates and butanol ($C_4H_{10}O$) as shown in FIG. 2. Without a reactant, dehydration and char formation is the preferred thermodynamic path as indicated in the shaded area. Decarbonation of forming butanol is not a spontaneous reaction under these conditions. It also illustrates that flash pyrolysis of biomass falls within the dehydration and char formation zone, synthesizing often up to 15%-30% char and the condensate bio oils with substantial amount of moisture/water. However with reactants #5 BaO, #4 SrO, and #3 CaO (a borderline), the decarbonation becomes the preferred thermodynamic pathway. According to the invention as illustrated in the modeling results in FIG. 2, some alkaline earth metal oxides—in particular #2 MgO and #1 BeO—are not sufficient to lower Gibbs Free Energy to prevent carbohydrates from dehydration and char formation. Actually, BeO raised the Gibbs free energy. Of particular note, not all alkaline earth metals are sufficient to act as reactants for this reason. This is important as the prior art may use MgO, $Mg(OH)_2$ and $MgCO_3$ as catalysts for flash pyrolysis/bio oils conversions from biomass. This graph confirms the unique nature of the present invention: the invention is clearly using a different mechanism than flash pyrolysis and catalyst additives therefore are not interchangeable with the reactants of the present invention. In the case of some reactants including CaO, lower or moderate temperatures less than 200° C. or 300° C. is preferred unlike flash pyrolysis at 500° C.

General equation of decarbonation of disaccharide ($C_{12}H_{22}O_{11}$) to form butanol ($C_4H_{10}O$) using alkaline earth metal oxides can be expressed as Eq. (3) where M denotes (alkaline earth) metal, and Eq (4) where no metal oxides are used.

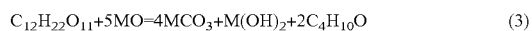

$$C_{12}H_{22}O_{11}+5MO=4MCO_3+M(OH)_2+2C_4H_{10}O \qquad (3)$$

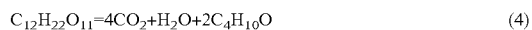

$$C_{12}H_{22}O_{11}=4CO_2+H_2O+2C_4H_{10}O \qquad (4)$$

Zone of dehydration and char formation is determined by the competing reaction Eq (5) of carbohydrate disaccharide (sucrose) to form water and carbon shown as the shade area in FIG. 1.

$$C_{12}H_{22}O_{11}=12C+11H_2O \qquad (5)$$

$$C_{12}H_{22}O_{11}5CaO=4CaCO_3+Ca(OH)_2+2C_4H_{10}O \qquad (6)$$

In illustration of the invention $C_4H_{10}O$ was chosen for thermodynamic modeling, and it by no means implies that $C_4H_{10}O$ that the consumed reactant as shown in Eq (6) is regenerated, and regeneration of consumed CaO as shown in Eq. (7) and (8)

$$CaCO_3=CaO+CO_2 \qquad (7)$$

$$Ca(OH)_2=CaO+H_2O \qquad (8)$$

The present invention is thermodynamic controlled chemical decarbonation by removal of $CO_2$ with a reactant that is a quite distinct from the common kinetic controlled catalytic conversions using CaO, MgO, $K_2O$, $Na_2O$, etc. as catalysts—the key differentiator is the order of magnitude in which the reactants are provided. Many of these chemicals have been widely used as catalysts in biomass conversion to bio oils or gasification. For example U.S. Pat. Nos. 8,344,194, 8,236,173, and 8,003,835 had disclosed inorganics including basic matters of CaO, $CaCO_3$, $K_2CO_3$, KOH, $Mg(OH)_2$, $NH_4OH$, etc. as catalysts for biomass pyrolysis, however their charge amounts typically were quite small at most up to few percentage of the biomass charge, i.e. few grams catalyst per kg biomass. The present invention discloses that the charge of reactant in the thermodynamic controlled decarbonation must be at a stoichiometric ratio to the $CO_2$ to be removed, or even at a greater excess. The present invention discloses that when CaO is used as reactant, its charge weight is in kilograms per every kg biomass feedstock, that is 2 to 4 orders of magnitude higher than those used as a catalyst, in order to lower reaction Gibbs Free Energy leading to the reaction path favoring a decarbonation.

The direct chemical synthesis of chemicals such as acetone, methyl ethyl ketone (MEK), etc. from carbohydrate feedstock of saccharides and cellulosic matters was not known, though biologic fermentation (Weizmann) ABE of producing acetone, ethanol and butanol had been practiced at industrious scales for some time until 1990s. Today acetone is produced commercially from petrochemicals. Cumene Process co-produced with phenol through acid catalyzed hydrolysis is a major source of acetone. The concept of chemical decarbonation of carbohydrate itself is not intuitive and has not been reported before, perhaps because there were no known functional groups in carbohydrates such as carboxylic group readily to be de-carboxylated, or to be de-carbonated and carbohydrate's tendency to de-hydration and charring upon heating.

The present invention presents an alternative route of making ketones such as acetone from chemical decarbonation of carbohydrates. Direct acetone formation from carbohydrate Eq. (1) falls within the de-hydration/charring zone (shaded area) as indicated in FIG. 2 and is not a thermodynamically favored reaction.

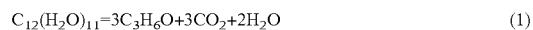

$$C_{12}(H_2O)_{11}=3C_3H_6O+3CO_2+2H_2O \qquad (1)$$

By reacting with a reactant such as CaO, the reaction (2) of carbohydrate forming acetone and carbonate becomes the favorite thermodynamically over the de-hydration/charring at temperatures up to 100° C. This decarbonation requires stoichiometric amount of reactants and is exothermic.

$$C_{12}(H_2O)_{11}+5CaO=3C_3H_6O+3CaCO_3+2Ca(OH)_2 \quad (2)$$

The present invention of chemical decarbonation of carbohydrates discloses a new route of making acetone previously unknown.

Accordingly the present invention clearly discloses that a chemical with strong chemical affinity toward $CO_2$ should be employed for decarbonation of carbohydrate such as disaccharide, starch and cellulose.

Accordingly the present invention clearly discloses reaction conditions to void dehydration or pyrolysis of carbohydrate such as disaccharide, starch and cellulose, these conditions to be voided are excessive temperatures, unbalanced charge of reactants not in stoichiometric ratios and wrong type of reactants.

Accordingly the present invention clearly discloses a reaction mechanism where the chemical decarbonation of carbohydrate to form oxygenated hydrocarbons according to Equations (2) and (3) must be maintained below a temperature threshold or an onset point. Sucrose's caramelization temperature is 186° C., which is close to its temperature threshold or its onset point. Therefore the decarbonation reaction of sucrose with a CaO as the reactant is preferably below 250° C., more preferably at 200° C. or below. Cooking at temperatures above 200° C. may lead to hydrocarbons or other side reactions of dehydration or pyrolysis. For corn starch, cellulose and hemicellulose, the temperature thresholds or the onset points for dehydration or pyrolysis are different and found to be higher than sugar sucrose, for example cellulose up to 300° C. It will be appreciated that this description is given for purposes of illustration and not by anyway of limitation of the present invention.

Introduction of a solvent such as a basic liquid matter of nitrogen containing heterocyclic compounds imidazoles, pyrazoles, pyrroles, pyrazines, pyridazines, pyrimidines and pyridines, their derivatives or ionic liquids, or simply liquid products combined with CaO as the reactant is also altering the temperature threshold or the onset point, causing it lower, for example for sucrose as low as 100° C. and for cellulose at 200° C. Again, it will be appreciated that this description is given for purposes of illustration and not by way of limitation of the present invention.

One with ordinary skills or knowledge in this field knows that there are many conventional ways or means in a chemical reactor to lower vapor pressure of products during cooking to speed up removal of products. Spurges or purge with inert gas such as nitrogen or argon, azetropic distillation with an inert solvent, cooking under reduced pressure or vacuum, an open vented reactor, use of chiller, a cold finger or condensation of volatile vapors, and a rotary reactor at constant rotation to substantially reduce product vapor trapped under powder CaO or $CaCO_3$. Again, it will be appreciated that this description is given for purposes of illustration and not by way of limitation of the present invention.

Biomass harvested naturally may contain substantial amount of water. Water may be present in the feedstock or formed during reaction. The impact of water upon decarbonation of carbohydrates forming acetone when a Reactant CaO is used can be examined and illustrated by Eq (9).

$$C_{12}H_{22}O_{11}+3Ca(OH)_2=3CaCO_3+3C_3H_6O(g)+4H_2O(g) \quad (9)$$

When water is at present, CaO reacts with water to form calcium hydroxide $Ca(OH)_2$ first as shown in Eq (10).

$$CaO+H_2O(g)=Ca(OH)_2 \quad (10)$$

Decarbonation reaction of Eq (9) using $Ca(OH)_2$ as a Reactant results in an upward shifting of its Gibbs Free Energy making it less favorable. As the Gibbs free energy raises the desired reaction pathway becomes less and less favorable. Water is not preferred when CaO is used as the reactant.

Figure 3:
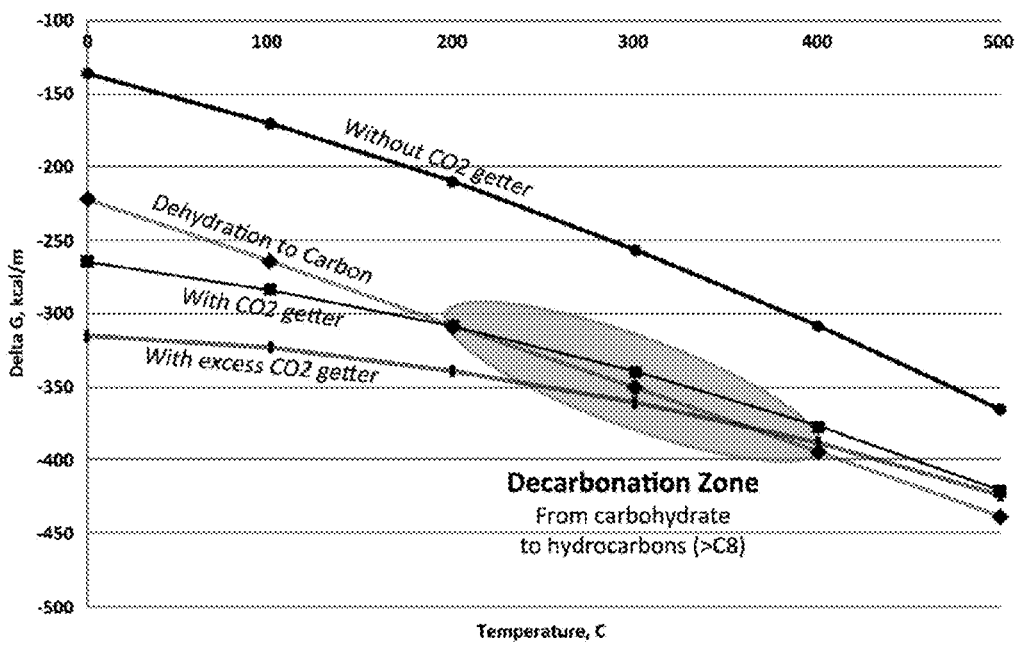
FIG. 3 illustrates the conversion of sucrose and calcium oxide into hydrocarbons in the chemical decarbonation zone of 200-400° C.

Taking sucrose as an example, the concept of chemical decarbonation of carbohydrates to hydrocarbon of $C_8H_{16}$ is better illustrated in FIG. 3—Gibbs Free Energies as a function of temperature: (11) decarbonation to $C_8H_{16}$ without a reactant; (12) dehydration or pyrolysis to carbon and water, (13) decarbonation by a reactant, (14) decarbonation by an excess amount of reactant.

Assuming disaccharide sucrose ($C_{12}H_{22}O_{11}$) as the feedstock, hydrocarbon $C_8H_{16}$ (a component of gasoline) as the product, the decarbonation reaction without a reactant is expressed in Equation (11), its negative Gibbs Free Energy indicates it is spontaneous.

$$C_{12}H_{22}O_{11}=4CO_2(g)+3H_2O(g)+C_8H_{16}(g) \; \Delta G=-205 \text{ kcal@200° C.} \quad (11)$$

However, dehydration or pyrolysis reaction of sucrose to form water and carbon of Eq. (12) is far more favorable thermodynamically than decarbonation Eq (11) with its more negative Gibbs Energy $$C_{12}H_{22}O_{11}=11H_2O(g)+12C \; \Delta G=-305 \text{ kcal@200° C.} \quad (12)$$

This suggests that prehistoric biomass deposits without the aid from a reactant in the earth crust preferably formed coal instead of forming hydrocarbon based petroleum.

When a chemical that strongly bonds with $CO_2$, a reactant can significantly lower Gibbs Energy of decarbonation as shown in equation (13) using CaO as an example of reactant.

$$C_{12}H_{22}O_{11}+4CaO=4CaCO_3+3H_2O(g)+C_8H_{16}(g) \\ \Delta G=-305 \text{ kcal@200° C.} \quad (13)$$

Chemical decarbonation of sucrose to hydrocarbons becomes thermodynamically favorable at temperature below 200° C. with CaO as reactant.

$$C_{12}H_{22}O_{11}+7CaO=4CaCO_3+3Ca(OH)_2+C_8H_{16} \; \Delta G=-340 \text{ kcal@200° C.} \quad (14)$$

An excess amount of reactant as indicated in Equation (14) further reduces Gibbs Energy, suppressing dehydration or pyrolysis up to temperatures of 380° C.

The oval zone in FIG. 3 predicts a chemical decarbonation zone of forming hydrocarbons: at reaction temperatures of above 200° C. but not exceeding 500° C. decarbonation of carbohydrate to hydrocarbon $C_8H_{16}$ is feasible and favorable while allowing suppression of de-hydration. Temperatures of chemical decarbonation forming hydrocarbons are generally lower than flash pyrolysis or gasification at 500° C. or higher.

It is worth noting that as shown in FIGS. 1 and 2 at lower decarbonation temperatures up to 200° C. oxygenated hydrocarbons such as acetone or butanol are likely formed, while in FIG. 3 at higher decarbonation temperatures up to 500° C., hydrocarbons are likely formed when reactant CaO is used.

The consumed reactant can be regenerated in a kiln, optionally along with a flow of miscellaneous chemicals recovered from the liquid product purification operations. Additionally, carbohydrate residual or ligno-cellulosic matter residual or bagasse or other convenient fuel can be combusted in the kiln for converting the consumed reactant back.

Theoretical yield of decarbonation per one ton of carbohydrate is 328 kg per 117 gallon for liquid hydrocarbons, or 510 kg per 163 gallon for acetone as product. Therefore chemical decarbonation is a cost effective way of converting cellulosic matters or ligno-cellulosic biomass.

The chemical decarbonation of carbohydrate of mono- and disaccharide sugar results in hydrophilic oxygenated liquids at temperatures below 200° C. Lower reaction temperatures less than 200° C. has been demonstrated to promote preferably formation of oxygenated hydrocarbons (ketones, -acetone etc.).

Accordingly the present invention clearly discloses that water is detrimental to decarbonation reaction of carbohydrates forming alcohols and acetone when a reactant of CaO is used. Biomass carbohydrates should be dried to remove free standing water, and water should not be used as a solvent. Excess amount of CaO can be added to the reactants to scavenge any remaining free water. Again, it will be appreciated that this description is given for purposes of illustration and not by way of limitation of the present invention. When a different kind of reactant, such as SrO, the presence of water has little impact.

Recovery of a solvent of nitrogen containing heterocyclic compounds imidazoles, pyrazoles, pyrroles, pyrazines, pyridazines, pyrimidines and pyridines, their derivatives or ionic liquids is precedent to the calcium carbonate regeneration. For lower boiling point of solvents, distillation at reduced pressures, or vacuum stripping with a third solvent such as water, acetone, alcohol or a lighter hydrocarbon is to be employed. For medium or higher boiling point solvents, besides vacuum distillation and vacuum stripping, other recovery means of solvent extraction is to be used. Again, it will be appreciated that this conceptual process mode is given for purposes of illustration and not by way of limitation of the present invention.

Unlike bioprocess or fermentation limiting alcohol concentration in aqueous solution 5% or 15% depending on enzyme or process, the disclosed invention of chemical decarbonation of carbohydrate with a reactant has no limitation on conversion. Given right conditions of sufficient cooking time, temperatures, blending/mixing and liquid product removal, the product yield approaches to the stoichiometric value, or near 100% or a complete conversion, for example for every 1.0 kg sucrose, yielding 0.51 kg acetone, and 0.49 kg $CO_2$ and water. Again, it will be appreciated that this description is given for purposes of illustration and not by way of limitation of the present invention.

Liquid products in the disclosed invention of chemical decarbonation of carbohydrate with a reactant are analyzed by GC/MA. Some components identified are subject to accuracy and resolution of instrument that needs further confirmation. Again, it will be appreciated that this description is given for purposes of illustration and not by way of limitation of the present invention.

Solid state reaction and liquid phase solid state reaction involve reactants being in solid states, or one of reactant being molten or in liquid state—liquid phase surrounding a solid core. Common examples of a solid state reactor are a rotary kiln for cement manufacturing, a screw reactor, a multiple hearth reactor and a bread bakery oven.

EXAMPLES

The following Examples are provided to illustrate certain aspects of the present invention and to aid those of skill in the art in practicing the invention. These Examples are in no way to be considered to limit the scope of the invention in any manner.

Component identification of the liquid product from the carbohydrate de-carbonation reaction was conducted by using Agilent 7890 GC with a Stabil-wax column, 60 m×0.25 mm×0.5 micro-m, 1/20 split injection couple with Agilent 5975 MSD (Mass Selective Detector).

Example 1

Conversion of Sucrose to Liquid and Gaseous Oxygenated Hydrocarbons with CaO

Sucrose (DOMINO®-brand cane sugar, 10 grams), and reagent-grade CaO powder (from Aldrich, 12 grams), were placed and grinded with pestle and mortar, and thoroughly mixed and sieved through a 350-mesh screen using ordinary methods and materials. The mixed blend was transferred and placed in a solid state reactor with an attached cooling finger to collect liquid. The reactor was placed inside an electric heating mantel or well controlled furnace with the cold finger attached to the reactor, but outside the hot zone, and chilled at temperature of 10° C.-12° C. that maintained the vapor pressure of the organic matter formed during reaction well below one atmosphere. Cold finger placement provided an open conduit to the reactor however minimized the liquid product flowing back into the reactor. A dry ice bath and a liquid nitrogen bath have been used also.

The solid state reactor was kept at 165° C. Within the first hour gaseous non-condensable product was formed and collected. A first portion of liquid was collected for 20 hours at 165° C. Then the reactor temperature was raised incrementally to 340° C. The remaining of liquid was collected. The organic liquid contained acetone, methyl ether ketone, cyclopantanones, acetyl, cyclopantenones, propanone hydroxyl, butanol, methyl hydroxyl furfural, other furans, etc. Different heating profiles were used. Fast heating at 20° C./minute to 160° C., and 5° C./minute to 200° C. and subsequent heating to 300° C. produced the liquid at yield of 82% with better collection of volatiles.

Figure 4:
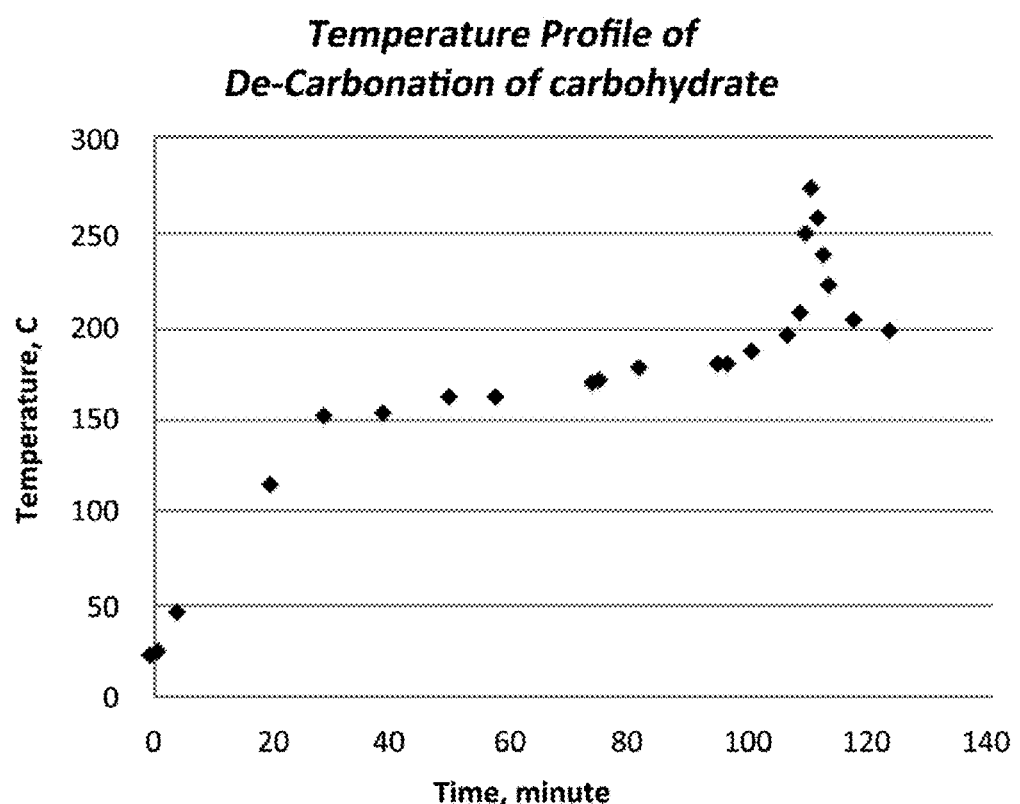
FIG. 4 illustrates a sucrose/CaO reaction temperature profile.

In one example, the stoichiometric-charged carbohydrate sucrose (10 gram) and reactant CaO (8.2 gram) were heated up electrically in a 100 mL reactor at two steady heating rates (30° C. to 150° C. @ 4° C./min, 150° C. to 200° C. @0.5° C./min)) with a thermocouple inserted inside the reactants to measure the real time reaction temperature as shown in FIG. 4. The exothermic reaction was evident when the temperature reached an onset point of 174° C., a sudden temperature increment of over 100° C. was recorded. The reaction liquid product contained 30% acetone, 15% methyl ethyl ketone, and others including acetol, furfurals, and many types of food flavors, and fragrances. The major products as identified using gas chromatography as described above are listed in the Table below.

| Product | % |
|---|---|
| acetone | 25-30 |
| 2-butanone | 10-15 |
| 1-hydroxyl2-propanone | 3-5 |
| 5-hydroxymethyl furfural | 3-5 |
| 3-hydroxyl2-butanone | 2-5 |
| 2-furancarboxaldehyde | 2-5 |
| 2-furanmethanol | 2-4 |
| 2-hydroxy-gamma-butyrolactone | 2-3 |
| ethanol | 1-3 |
| 2,3-butanedione | 1-3 |
| acetic acid | 1-3 |
| 1-acetyl oxy-2-propan one | 1-3 |
| cyclopentanone | 1-2 |
| 2-cyclopenten-1-one | 1-2 |
| 3-methyl-2-cyclopenten-1-one | 1-2 |
| 2-methyl-2-cyclopenten-1-one | 1-2 |
| 2,3-methyl-2-cyclopenten-1-one | 1-2 |
| 1,2-propanediol | 1-2 |
| 5-methyl-2-furancarboxaldehyde | 1-2 |
| 1,2-ethanediol | 1-2 |

-continued

| Product | % |
| --- | --- |
| 1,2butanediol | >1 |
| 2-hydroxyl-3-methyl-2-cyclopentanone | 0.5-1 |
| acetaldehyde | 0.1-10 |
| 2-propanol | 0.1-1 |
| 2-methylcyclopentanone | 0.1-1 |
| 3-methylcyclopentanone | 0.1-1 |
| 1-butanol | 0.1-1 |
| 2,5 dimethyl2-cyclopentanone | 0.1-1 |
| 3-methyl-3-hexen-2-one | 0.1-1 |
| 3-methyl-2(5H)-furanone | 0.1-1 |
| 2-methyl-tetrahydrofuran-3-one | 0.1-1 |
| hydroxydimethylfuranone | 0.1-1 |
| 4-hydroxy-5-oxohexanoic acid lac | 0.1-1 |

Example 2

Conversion of Sucrose to Liquids and Gaseous Oxygenated Hydrocarbons with CaO and Polyethylene Glycol Sucrose (DOMINO® cane sugar, 10 grams), and reagent grade CaO powder (from Aldrich, 10 grams), were combined and grinded with pestle and mortar, thoroughly mixed, and sieved through a 350-mesh screen. Twenty grams of polyethylene glycol (average MW 400) was then added to the mixture and blended to achieve a uniform slurry. The mixed slurry was transferred and placed in a solid state reactor with an attached cooling finger to collect liquid. The reactor was placed inside an oven or well controlled bakery furnace with the cold finger attached to the reactor but outside the hot zone chilled at temperature of 10° C.-12° C. that maintained the vapor pressure of organic matter formed during reaction well below one atmosphere. Cold finger placement provided an open conduit to the reactor however minimized the liquid product flowing back into the reactor.

At the top of cold finger a gas vent allowing the gas formed during reaction to be passed through a gas venting tubing to a graduated cylinder was placed upside down prefilled with water in a water bath so that only water insoluble hydrocarbons was collected in the cylinder. Once formation of volatile gas ceases, the gas venting tubing was promptly disconnected from the water bath so that no water was sucked back into the cold finger.

The solid state reactor was kept at 165° C. Within the first hour gaseous non-condensable was formed and collected. A colorless liquid was collected for 30 hours at 165° C.

Example 3

Conversion of Sucrose to Liquids and Gaseous Oxygenated Hydrocarbons with CaO and 1-Methyl Imidazole Sucrose (DOMINO® cane sugar, 10 grams), and reagent grade CaO powder (from Aldrich, 15 grams), were combined and grinded with pestle and mortar, thoroughly mixed, and sieved through a 350-mesh screen. The mixed blend was added 15 grams of 1-methyl imidazole (Source) and blended into a uniform slurry. The slurry was transferred to a solid state reactor with an attached cooling finger to collect liquid. The reactor was placed inside an oven or well controlled bakery furnace with the cold finger attached to the reactor but outside the hot zone chilled at temperature of 10°-12° C. that maintains vapor pressure of organic matter formed during reaction well below one atmosphere pressure. Cold finger placement provided an open conduit to the reactor however minimized the liquid product flowing back into the reactor.

At the top of cold finger a gas vent allowing the gas formed during reaction to be passed through a gas venting tubing to a graduated cylinder was placed upside down prefilled with water in a water bath so that only water insoluble hydrocarbons was collected in the cylinder. Once formation of volatile gas ceased, the gas venting tubing was promptly disconnected from the water bath so that no water was sucked back into the cold finger. In some cases water trap was not used.

The solid state reactor was kept at 165° C. Within the first hour gaseous non-condensable was formed and collected. A first portion of liquid was collected for 12 hours at 165° C. Then the reactor was raised incrementally to 340° C. The remaining of liquid was collected. The organic liquid contained ethanol, acetone, butanone, dimethyl furan and 1-methyl imidazole etc.

Example 4

Conversion of Cellulose to Liquids with CaO

Cellulose (from NutnCology, 10 grams), and reagent grade CaO powder (from Aldrich, 12 grams), were placed and ground with pestle and mortar, thoroughly mixed and sieved through a 350-mesh screen. The mixed blend was transferred to a solid state reactor with an attached cooling finger to collect liquid. The reactor was placed inside an oven or well controlled bakery furnace with the cold finger attached to the reactor but outside the hot zone chilled at temperature of 10° C.-12° C. that maintains vapor pressure of the organic matter formed during reaction well below one atmosphere pressure. Cold finger placement provided an open conduit to the reactor however minimized the liquid product flowing back into the reactor.

At the top of cold finger a gas vent allowing the gas formed during reaction to be passed through a gas venting tubing to a graduated cylinder was placed upside down prefilled with water in a water bath so that only water insoluble hydrocarbons was collected in the cylinder. Once formation of volatile gas ceases, the gas venting tubing was promptly disconnected from the water bath so that no water was sucked back into the cold finger. In some setups no water trap was used.

The solid state reactor was kept at 165° C. A first portion of liquid was collected for 5 days at 165° C. Then the reactor was raised incrementally to 340° C. for additional two days. The remaining of liquid was collected.

Different heating profiles were used. 4 hour heating to 350° C. produced liquid at yield of 65%. The organic liquid contained acetone, methyl hydroxyl furfural, and lovaglycosane, etc.

Example 5

Conversion of Cellulose to Liquids with CaO and 1-Methyl Imidazole

Cellulose (Source, 10 grams), and reagent grade CaO powder (Source, 12 grams), were placed and ground with pestle and mortar, thoroughly mixed and sieved through a 350-mesh screen. To the mixture was added 15 grams of liquid 1-methyl imidazole (Source), and the combination was blended. The slurry within minutes turned to gel and completely solidified. The solid was transferred and placed in a solid state reactor with an attached cooling finger to collect liquid. The reactor was placed inside an oven or well controlled bakery furnace with the cold finger attached to the reactor but outside the hot zone chilled at temperature of 10°-12° C. that maintained the vapor pressure the of organic matter formed during reaction well below one atmosphere. Cold finger placement provided an open conduit to the reactor however minimized the liquid product flowing back into the reactor.

At the top of cold finger a gas vent allowing the gas formed during reaction to be passed through a gas venting tubing to a graduated cylinder was placed upside down prefilled with water in a water bath so that only water insoluble hydrocarbons was collected in the cylinder. Once formation of volatile gas ceases, the gas venting tubing was promptly disconnected from the water bath so that no water was sucked back into the cold finger. In some setups no water trap was used.

The solid state reactor was kept at 165° C. Within the first hour gaseous non-condensable was formed and collected. A first portion of liquid was collected for 20 hours at 165° C. Then the reactor was raised incrementally to 340° C. for additional 10 hours. The remaining of liquid was collected that contained acetone, butanone, and 1-methyl imidazole.

Different temperature profiles were used including the reaction time as short as 2 hours.

Example 6

Conversion of Sucrose to Oxygenated Hydrocarbons and Hydrocarbons with CaO

Sucrose (DOMINO® cane sugar, 10 grams), and reagent grade CaO powder (Aldrich, 12 grams), were placed and ground with pestle and mortar, thoroughly mixed and sieved through a 350-mesh screen. The mixture was transferred and placed in a solid state reactor with an attached cooling finger to collect liquid. The reactor was placed inside an oven or well controlled bakery furnace with the cold finger attached to the reactor but outside the hot zone chilled at temperature of 10°-12° C. that maintained the vapor pressure of the organic matter formed during reaction well below one atmosphere. Cold finger placement provided an open conduit to the reactor however minimized the liquid product flowing back into the reactor.

At the top of cold finger a gas vent allowing the gas formed during reaction to be passed through a gas venting tubing to a graduated cylinder was placed upside down prefilled with water in a water bath so that only water insoluble hydrocarbons was collected in the cylinder. Once formation of volatile gas ceases, the gas venting tubing was promptly disconnected from the water bath so that no water was sucked back into the cold finger. In some setups no water trap was used.

The solid state reactor was kept at 165° C. Within the first hour gaseous non-condensable was formed and collected. A first portion of liquid was collected for 20 hours at 165° C. Then the reactor was raised incrementally to 300° C. The liquid was collected and found to be hydrophilic The reactor was further heated to 500° C., and the remaining liquid was collected. The liquid was found to be hydrophobic forming thin oily film on water surface, hydrocarbon-like not miscible with the first portion that consists of oxygenates collected below 300° C.

Example 7

Conversion of Cellulose to Oxygenated Hydrocarbons and Hydrocarbons with CaO and Ionic Liquid As in Example 5, an ionic liquid butyl methyl imidazolium chloride was used to replace 1-methyl imidazole. The reaction product liquid collected contained acetone, butanone and derivatives from the ionic liquid.

Example 8

Conversion of Sucrose with MgO

As in example 1, CaO was replaced by MgO, the carbohydrate sucrose was converted to liquid containing organic components such as acetone, however water content was substantially high, evidenced by freezing at −10° C.

Example 9

Conversion of Carbohydrate Sucrose with CaO at Various Charge Ratios

As in Example 1, sucrose and CaO were charged and reacted with each other, however the charge ratios were varied. The stoichiometric ratio of CaO to sucrose is 0.82:1 by weight. All runs were conducted at reactor temperature of 250° C.:

| 0.25:1 | 0.5:1 | 0.75:1 | 1:1 | 1.25:1 | 1.5:1 | 2:1 |
|--------|-------|--------|-----|--------|-------|-----|

When the charge ratios were to be from 0.75:1 to 1.25:1, it had resulted in the product yields 75% to 83%. Compositions of the liquid products were found to be similar to ones in Example 1, rich in acetone. Once CaO charge was reduced to less than 0.5:1, substantial char formations were observed. Excess charge of CaO at 2:1 had resulted in a substantial reduction of the product yield to merely 32%.\

CONCLUSION

The present invention based on principles of thermodynamics has solved the long standing problem of converting carbohydrate into liquids and gas by a single chemical process of promoting decarbonation by suppressing dehydration, pyrolysis, or syngas formation without using the relatively slow biological fermentation process. The process is achieved by adding a reactant which may or may not be as catalyst in a stoichiometric ratio, such that the reactant causes the reaction to proceed thermodynamically in favor of decarbonation forming carbonate as a byproduct and organics without char formation.

It will be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment and for particular applications, those skilled in the art will recognize that its usefulness is not limited thereto and that the present invention can be beneficially utilized in any number of environments and implementations where the skilled artisan would find it desirable. Accordingly, the claims set forth below should be construed in view of the full breadth and spirit of the invention as disclosed herein.

The invention claimed is:

1. A method for the de-carbonation of a carbohydrate to form acetone or 2-butanone therefrom, comprising: combining a carbohydrate selected from the group consisting of: mono-, di-, oligo-, and poly-saccharides, starches, cellulose, hemicellulose, and lingo-cellulosic biomass with a material selected from the group consisting of: oxides and hydroxides of alkaline-earth metals, said carbohydrate and said material being combined in a material:carbohydrate ratio of between about 0.2:1 and about 5:1 by stoichiometry and a temperature between about 100° C. and about 450° C., to form said acetone or 2-butanone.

2. The method of claim 1, wherein said temperature is between about 165° C. and about 300° C.

3. The method of claim 2, wherein said temperature is between about 165° C. and about 250° C.

4. The method of claim 3, wherein said temperature is between about 165° C. and about 200° C.

5. The method of claim 1, wherein said ratio is between about 0.5:1 and about 2:1.

6. The method of claim 5, wherein said ratio is between about 0.75:1 and about 1.2:1.

7. The method of claim 1, wherein said material is an alkaline-earth oxide.

8. The method of claim 5, wherein said alkaline-earth oxide is CaO.

9. The method of claim 8, wherein said hydrocarbon and said material are combined in a material:carbohydrate ratio of between about 0.5:1 and about 2:1 by weight.

10. The method of claim 9, wherein said temperature is between about 150° C. and about 350° C.

11. The method of claim 10, wherein said temperature is between about 165° C. and about 300° C.

12. The method of claim 11, wherein said temperature is between about 165° C. and about 250° C.

13. The method of claim 12, wherein said temperature is between about 165° C. and about 200° C.

14. The method of claim 9, wherein said ratio is between about 0.75:1 and about 1.5:1.00.

15. The method of claim 14, wherein said ratio is between about 0.75:1 and about 1.25:1.

16. The method of claim 15, wherein said carbohydrate is a di-saccharide.

17. The method of claim 16, where said carbohydrate is sucrose.

* * * * *